United States Patent [19]

Ecke, Jr.

[11] Plant 4,821

[45] Feb. 2, 1982

[54] POINSETTIA NAMED V-10 PINK

[75] Inventor: Paul Ecke, Jr., Encinitas, Calif.

[73] Assignee: Paul Ecke Ranch, Encinitas, Calif.

[21] Appl. No.: 185,123

[22] Filed: Sep. 5, 1980

[51] Int. Cl.[3] ..... A01H 5/00

[52] U.S. Cl. ..... Plt./86

[58] Field of Search ..... Plt./86

*Primary Examiner*—Robert E. Bagwill

*Attorney, Agent, or Firm*—Rummler and Snow

[57] ABSTRACT

A new poinsettia cultivar which is substantially the same as the variety Gutbier's V-10 (U.S. Plant Pat. No. 4,235) with respect to form, growth and blooming habits, differing only that this new variety has a pleasing and distinctive pink coloration of its bracts.

1 Drawing Figure

BACKGROUND OF THE NEW PLANT

My new poinsettia plant originated as a mutation of its parent, the red variety Gutbier's V-10, this new plant resulting from many trials carried on by me at Encinitas, Calif., with the object of obtaining new and desirable poinsettia varieties for the commercial market. This plant was selected by me because of its unique pink coloration and was propagated by me, by means of cuttings, at my greenhouse in Encinitas, Calif. Subsequently, I subjected this new plant to successive generations of propagation and found that its unique and distinctive characteristics held true from generation to generation and appeared to be firmly fixed.

Propagation of this new pink variety of poinsettia plant, by means of cuttings, is now being done on a commercial scale at Encinitas, Calif.

DESCRIPTION OF THE DRAWINGS

This new variety of poinsettia plant is illustrated by the accompanying full color photographic drawings, the upper one of which shows a full face view of the mature bloom of this plant and the lower one is a view showing a potted plant of this variety in full bloom.

DESCRIPTION OF THE NEW PLANT

The following is a detailed description of my new variety of poinsettia plant as observed at Encinitas, Calif., with color designations according to the R.H.S. Colour Chart published by The Royal Horticultural Society of London, England.

THE PLANT

Origin: Mutation.

Parentage: Gutbier's V-10 (U.S. Plant Pat. No. 4,235).

Classification:

*Botanic.*—*Euphorbia pulcherrima.*

*Commercial.*—Greenhouse poinsettia.

Form: Shrub.

Height: Medium short.

Growth habit:

*As a single stem.*—Upright and vigorous with self branching side shoots; usually will not require a growth regulator.

*As a branched plant.*—Upright with very many stems producing a bushy, full appearance.

Growth rate: Very fast with rooting occurring within 10 to 15 days under automatic mist and the plant blooming in 8 to 9 weeks at a night time temperature of 14° to 16° C.

Foliage: Alternate, horizontal, with medium persistence and in normal abundance.

*Leaf size.*—Medium. About 3 to 6 inches long and about $2\frac{1}{2}$ to $4\frac{1}{2}$ inches wide.

*Leaf shape.*—Ovate, with acuminate apex and substantially entire margins.

*Aspect.*—Upper side — smooth and medium glossy. Under side — dull with ordinary venation.

*Color.*—Upper side — RHS 137A. Under side — RHS 137A but a slight shade lighter.

*Retention.*—The foliage lasts well when kept at a low room temperature, i.e. below 20° C., and with good light intensity.

Bracts: Ordinarily about 12 to 16 in number and in overlapping arrangement with a tight center which provides a full effect. Mature and over-ripe blooms develop increasing numbers of bracts, often as many as 25 to 30, which cascade in two or three layers thereby increasing the fullness of the bloom. Many of the bracts have a unique arched appearance.

Size: Varies; up to about 6 inches long and about 4 inches wide.

Shape: Ovate, with acuminate apex and substantially entire margin. Small bracts are elliptic in shape.

Color:

*Upper side.*—RHS 51A to 51B. Color varies depending upon maturity.

*Under side.*—RHS near 180D.

Ribs and veins: Light green in color appearing on the under side of the bracts.

This new poinsettia variety is substantially identical in all important respects with its parent, the red variety Gutbier's V-10 (U.S. Plant Pat. No. 4,235), the new plant differing from its parent only with respect to the distinctive pink coloration of its bracts, which provides a new and commercially attractive addition to the range of poinsettia plants available to the commercial market.

I claim:

1. A new and distinctive poinsettia cultivar, substantially as herein shown and described, characterized by the attractive pink coloration of its many bracts displayed in overlapping arrangement about a tight center to provide a full effect, and by its identity with the variety Gutbier's V-10 with respect to size, appearance and growth, and blooming habits.

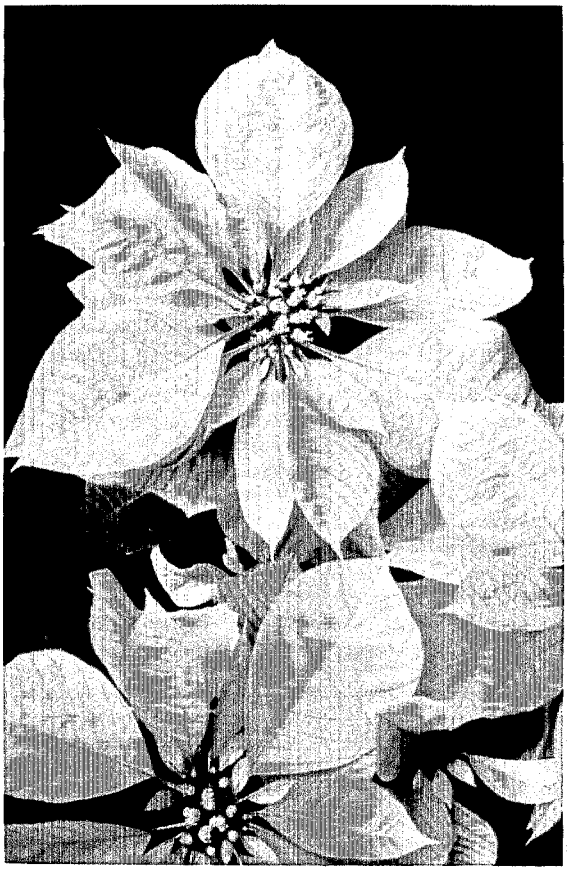
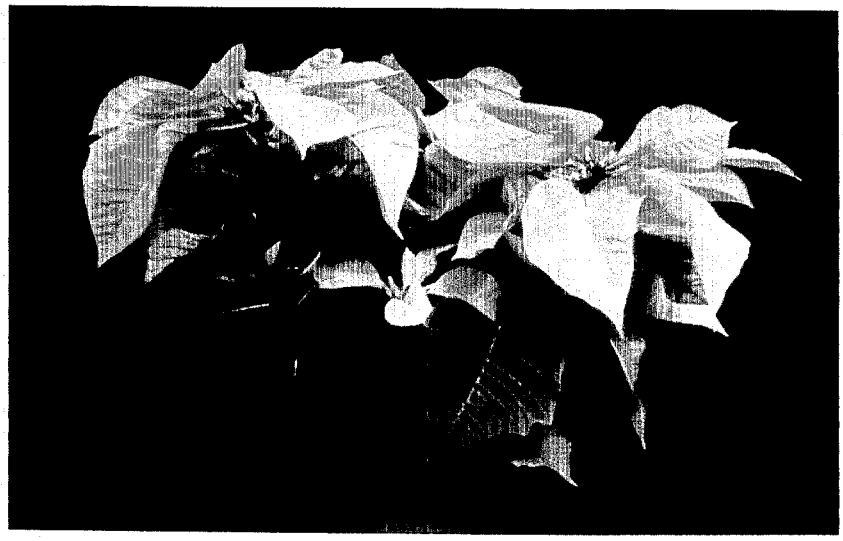

* * * * *